(12) United States Patent
Cassone

(10) Patent No.: US 7,077,815 B1
(45) Date of Patent: Jul. 18, 2006

(54) METHOD FOR TREATING BODY TISSUE DISEASE WITH ACOUSTIC WAVES

(76) Inventor: Alphonse Cassone, 2626 S. Rainbow Blvd., #109, Las Vegas, NV (US) 89146

( * ) Notice: Subject to any disclaimer, the term of this patent is extended or adjusted under 35 U.S.C. 154(b) by 927 days.

(21) Appl. No.: 09/619,357

(22) Filed: Jul. 19, 2000

(51) Int. Cl.
*A61H 23/00* (2006.01)

(52) U.S. Cl. .............................. 601/47; 601/55; 601/46; 128/898

(58) Field of Classification Search ................. 601/46, 601/47, 48, 49, 55, 56
See application file for complete search history.

(56) References Cited

U.S. PATENT DOCUMENTS

| | | | | |
|---|---|---|---|---|
| 3,585,991 | A | * | 6/1971 | Balamuth .................... 604/157 |
| 4,945,901 | A | * | 8/1990 | Burcke, Jr. ................. 601/157 |
| 5,097,821 | A | * | 3/1992 | Eakin |
| 5,314,403 | A | * | 5/1994 | Shaw |
| 5,695,455 | A | * | 12/1997 | Alton, Jr. et al. |
| 5,727,556 | A | * | 3/1998 | Weth et al. .................. 128/660 |

FOREIGN PATENT DOCUMENTS

| | | | | |
|---|---|---|---|---|
| DE | | 233074 | * | 2/1986 |
| DE | | 19731070 | * | 2/1999 |
| EP | | 465870 | * | 1/1992 |
| EP | | 0891761 | * | 1/1999 |
| WO | WO 98/27923 | | * | 8/1998 |

* cited by examiner

*Primary Examiner*—Danton DeMille
(74) *Attorney, Agent, or Firm*—Harry M. Weiss; Jeffrey Weiss; Weiss & Moy, P.C.

(57) ABSTRACT

A method for treating inflammatory musculoskeletal connective tissue disorders by exposing the sufferer to acoustic waves from a transducer immersed in liquid. The person is preferably placed between one and twenty feet from the wave source, and is preferably exposed to waves at a frequency of about 600 Hertz for approximately twenty five minutes.

17 Claims, 1 Drawing Sheet

METHOD FOR TREATING BODY TISSUE DISEASE WITH ACOUSTIC WAVES

FIELD OF THE INVENTION

This invention relates generally to methods for treating disease and, more specifically, to a method for treating diseases affecting body tissue through the use of acoustic waves.

BACKGROUND OF THE INVENTION

There are numerous disorders that effect the musculoskeletal connective tissue of human and animal bodies. These include the following: arthritis (including rheumatoid arthritis, osteoarthritis, joint pain, and psoriatic arthritis); menstruation related disorders (including cramping and endometrial pain); polymyositis; muscle disorders; and stress. These different disorders and diseases share in common the fact that they may cause inflammation of the musculoskeletal connective tissue, resulting in pain and discomfort. The effective treatment of these disorders, and the pain and discomfort they cause, is obviously a matter for concern.

Some background information regarding these disorders and diseases, their causes, their affects on the body, and their treatments, illustrate the foregoing:

Arthritis

The term "arthritis" means joint inflammation; i.e., swelling, redness, heat, and pain caused by tissue injury or disease in the joint. Types of arthritis include osteoarthritis, rheumatoid arthritis, and psoriatic arthritis.

Osteoarthritis, the most common form of arthritis, affects more than 20 million adults in the United States. It primarily affects cartilage, and occurs when cartilage begins to fray, wear and decay. In extreme cases, the cartilage may wear away entirely, leaving a bone-on-bone joint. Osteoarthritis can cause joint pain, reduced joint motion, loss of function, and disability. Disability results most often when the disease affects the spine and the weight-bearing joints.

Rheumatoid arthritis is an inflammatory disease of the synovium, or lining of the joint, that results in pain, stiffness, swelling, deformity, and loss of function in the joints. Inflammation most often affects joints of the hands and feet. More than two million people in the United States have rheumatoid arthritis.

Psoriatic arthritis occurs in some patients with psoriasis, a common scaling skin disorder. Psoriatic arthritis often affects the joints at the ends of the fingers and is accompanied by changes in the fingernails and toenails. Some people suffering from psoriatic arthritis also have spinal involvement.

Other than infectious arthritis, there is no known cure for arthritis. Current treatments only work to limit the symptoms of this disease. Treatments include rest and relaxation, exercise, hot and cold therapy, hydrotherapy, mobilization therapy, relaxation therapy, proper diet, instruction about the proper use of joints and ways to conserve energy, pain relief methods, assistive devices such as splints or braces, surgery, and medication. The medications used include analgesics, nonsteroidal anti-inflammatory drugs, acetaminophen, and corticosteroids.

Bursitis

Bursitis is a condition involving inflammation of the bursae, small, fluid-filled sacs that help reduce friction between bones and other moving structures in the joints. The inflammation may result from arthritis in the joint or injury or infection of the bursae. Bursitis produces pain and tenderness and may limit the movement of nearby joints.

Menstrual Cramping and Endometrial Pain

Menstrual pain, dysmenorrhea, includes as one of its symptoms menstrual cramps. Dysmenorrhea is related to prostaglandin production. Current treatments include oral combined contraceptives, beta-blockers, nonsteroidal anti-inflammatory drugs, psychotherapeutic methods, and cervical dilatation.

Endometriosis is a common disease, affecting about 10 to 20 percent of American women of childbearing age. In endometriosis, tissue that looks and acts like endometrial tissue (the tissue that lines the inside of the uterus) is found outside the uterus, usually inside the abdominal cavity. At the end of every menstrual cycle, when hormones cause the uterus to shed its endometrial lining, endometrial tissue growing outside the uterus will break apart and bleed. However, unlike menstrual fluid from the uterus, which is discharged from the body during menstruation, blood from the misplaced tissue has no place to go. Tissues surrounding the area of endometriosis may become inflamed or swollen. The inflammation may produce scar tissue around the area of endometriosis. These endometrial tissue sites may develop into what are called "lesions," "implants," "nodules," or "growths."

The most common symptom of endometriosis is pain, especially excessive menstrual cramps (dysmenorrhea) which may be felt in the abdomen or lower back or pain during or after sexual activity. Rarely, the irritation caused by endometrial implants may progress into infection or abscesses causing pain independent of the menstrual cycle. Endometrial patches may also be tender to touch or pressure, and intestinal pain may also result from endometrial patches on the walls of the colon or intestine.

Current treatment for endometriosis includes pain medication, hormone treatment, and hormone suppression treatment. Hormone suppression treatment shuts off ovulation, and thus is only available to those women who are not seeking to become pregnant.

Polymyositis

Polymyositis is an inflammatory muscle disease that causes varying degrees of decreased muscle power. The most common symptom is muscle weakness, usually affecting those muscles that are closest to the trunk of the body. Eventually, patients have difficulty rising from a sitting position, climbing stairs, lifting objects, or reaching overhead. In some cases, muscles not close to the trunk of the body may also be affected later in the course of the disease. Trouble with swallowing (dysphagia) may occur. Occasionally, the muscles ache and are tender to touch. Patients may also feel fatigue and discomfort and have weight loss or a low-grade fever.

Treatment for polymyositis generally consists of a steroid drug called prednisone. For patients in whom prednisone is not effective, immunosuppressants such as azathioprine and methotrexate may be prescribed. Physical therapy is usually recommended to preserve muscle function and avoid muscle atrophy. Some cases of polymyositis respond to therapy, while the disease is usually more severe and resistant to therapy in patients with cardiac or pulmonary problems.

Muscle Disorders

The muscles of the body that can be voluntarily contracted are vulnerable to a variety of muscle disorders, including cramping, spasms, and tension. A muscle spasm occurs when a muscle contracts involuntarily. A sustained and forceful spasm is a muscle cramp. Muscle cramps generally last from a few seconds to fifteen minutes, and can affect a part of a muscle, a whole muscle, or a group of muscles. They are extremely common—affecting almost every person at some time.

There are four major types of skeletal muscle cramps—true cramps, tetany, contractures, and dystonic cramps. True cramps are the most common type of cramp. They are caused by the hyperexcitability of the nerves that stimulate the muscles. Tetany occurs when all of the body's nerve cells are activated, stimulating the muscles and causing spasms or cramps throughout the body. Dystonic cramps are where muscles that are not needed for the intended movement are stimulated to contract.

Cramps can be caused by a variety of factors, including as a protective mechanism following an injury, associated with the vigorous use of muscles and muscle fatigue, dehydration, body fluid shifts, low blood calcium, low blood magnesium, low potassium, medication, and vitamin deficiencies. Treatments include stretching of the cramped muscles, therapeutic doses of botulism toxin, and quinine. (Quinine, however, has been shown to cause birth defects and miscarriages.) Where cramps are associated with an underlying medical condition, treatment focuses on the underlying condition.

Stress

Stress is the reaction of animals to deleterious forces, such as abnormal states that tend to disturb their normal physiologic equilibrium. In response to stress, the pituitary gland and other systems within the body release hormones and trigger other responses to muster the body's defenses. Symptoms associated with stress include, among others, musculo-skeletal problems.

It should be clear then that each of these disorders and diseases presents a problem to those who are afflicted, and that safe and effective treatments are desirable. With respect to treatment methods, non-invasive, non-surgical techniques are generally preferred to surgery. Moreover, safe non-chemical treatments are generally preferred to the use of medications, which can have foreseen or unforeseen side-effects on the body. While the individual disorders listed here have different causes, the fact that they all can affect the musculoskeletal system raises the possibility that a single treatment could potentially work for each of these disorders. The present invention is directed to a treatment for each of these disorders—a treatment that is non-invasive, non-surgical, and non-chemical.

In U.S. Pat. No. 5,132,942, issued to applicant herein, a low frequency electroacoustic transducer (the "Cassone Transducer") is disclosed. According to U.S. Pat. No. 5,132, 942, the Cassone Transducer could be used to efficiently disperse emulsions, chemical and other wastes, and the like for recycling and environmental enhancement. The Patent does not disclose the use of the Cassone Transducer for medical purposes. It is to that use that the current invention is directed.

SUMMARY OF THE INVENTION

It is an object of this invention to provide a non-invasive method for treating diseases affecting body tissue.

It is a further object of this invention to provide a non-surgical method for treating diseases affecting body tissue.

It is a still further object of this invention to provide a non-chemical method for treating diseases affecting body tissue.

It is a still further object of this invention to provide a method for treating diseases affecting body tissue through the use of acoustic waves.

BRIEF DESCRIPTION OF THE PREFERRED EMBODIMENTS

In accordance with one embodiment of the present invention, a method for treating inflammatory musculoskeletal connective tissue disorders is disclosed. The method comprises the steps of: providing a low frequency sonic transducer; positioning a person having an inflammatory musculoskeletal connective tissue disorder a therapeutically beneficial distance from the low frequency sonic transducer; and exposing the person for a therapeutically beneficial period of time to acoustic waves from the low frequency sonic transducer at a therapeutically beneficial frequency.

In accordance with another embodiment of the present invention, a method for treating inflammatory musculoskeletal connective tissue disorders is disclosed. The method comprises the steps of: providing a low frequency sonic transducer; positioning a person having an inflammatory musculoskeletal connective tissue disorder between approximately one foot and approximately twenty feet from the low frequency sonic transducer from the low frequency sonic transducer; and exposing the person for between approximately fifteen minutes and forty-five minutes to acoustic waves from the low frequency sonic transducer at approximately six hundred Hertz.

In accordance with still another embodiment of the present invention, a method for treating inflammatory musculoskeletal connective tissue disorders is disclosed. The method comprises the steps of: providing a low frequency sonic transducer; immersing the low frequency sonic transducer in a liquid-containing container; positioning at least a portion of a body a person having an inflammatory musculoskeletal connective tissue disorder in the liquid-containing container; and exposing the person for between approximately fifteen minutes and forty-five minutes to acoustic waves from the low frequency sonic transducer at approximately six hundred Hertz.

DETAILED DESCRIPTION OF THE PREFERRED EMBODIMENTS

The present invention is concerned with an improved method for treating inflammatory musculoskeletal connective tissue disorders. Such disorders include but are not limited to: arthritis (including rheumatoid arthritis, osteoarthritis, joint pain, and psoriatic arthritis); bursitis; menstruation related disorders (including cramping and endometrial pain); polymyositis; muscle disorders; and stress.

Figure 2:
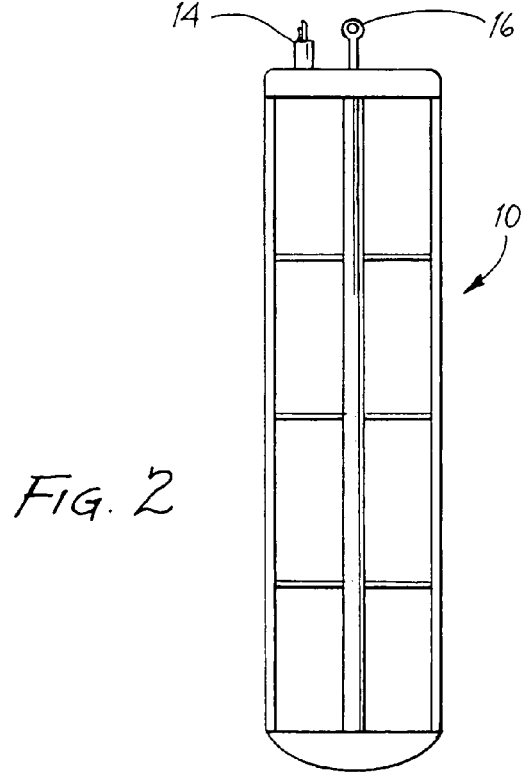
FIG. 2 is a side, cross-sectional view of an electroacoustic transducer of the type preferably used in the method of the present invention.

The method begins with the placement of a transducer 10 like the Cassone Transducer in a container 12 containing water or another liquid. The container 12 preferably has a volume ranging from one to five hundred gallons, with a volume of between five and fifty five gallons regarded as particularly preferred and a volume of approximately fifty gallons regarded as optimal. Preferably, the transducer 10 is modified slightly from the Cassone Transducer shown in U.S. Pat. No. 5,132,942 by the addition of a water-tight electrical connector 14 to replace the coaxial supply line and terminal 10 shown in FIG. 2 of U.S. Pat. No. 5,132,942, and an eye-bolt 16 to replace the pair of lift members 12 shown in FIG. 2 of U.S. Pat. No. 5,132,942. These modifications are intended to facilitate the dedicated use of the transducer 10 in a liquid environment, with the water-tight electrical connector 14 providing increased safety and the eye-bolt 16 making more easy the removal of the transducer 10 from the container 12. (While a modified Cassone Transducer as described herein is preferred for the transducer 10, any transducer capable of operating in a liquid environment and of generating acoustic waves at frequencies within the ranges described below would suffice.)

Figure 1:
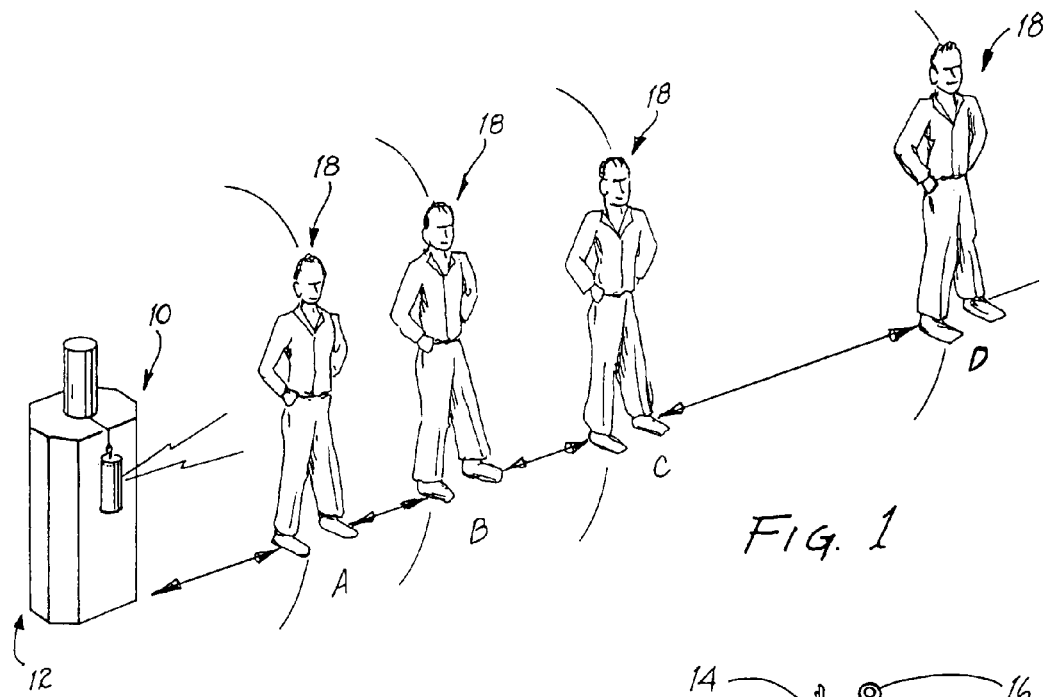
FIG. 1 is a perspective view of the practicing of the method of the present invention, with the positioning of a person at varying distances from an electroacoustic transducer.

Referring now to FIG. 1, a person 18 suffering from a musculoskeletal connective tissue disorders is positioned near the container 12 with the transducer 10 therein. (While a person 18 is shown as a human, the term "person" as used herein is intended to include animals and humans alike.) The person 18 may be positioned at any distance relative to the transducer 10/container 12 that is determined to be therapeutically beneficial. Tests have indicated that benefit is provided within a range of from approximately one foot to approximately twenty feet—though benefit may be provided outside of this range as well as at any point within this range. Distance A is intended to represent one foot of distance, distance B represents five feet of distance, distance C represents 10 feet of distance, and distance D represents 20 feet of distance.

While FIG. 1 illustrates a person 18 positioned at different points to one side of the transducer 10, it should be noted that the transducer 10 is omni-directional, such that a person 18 could be positioned on any side of the transducer 10—or two or more persons 18 could be positioned on different sides of the transducer 10 simultaneously. Indeed, preferably, persons 18 are placed in chairs surrounding the transducer 10, and receive treatment in this relatively comfortable orientation.

The person 18 should be exposed to acoustic waves from the transducer 10 at any frequency that is determined to be therapeutically beneficial. Tests have indicated that benefit is provided within a range of from one to one thousand Hertz, with particularly good results obtained between four hundred and eight hundred Hertz and optimal results obtained at approximately six hundred Hertz.

The person 18 should be exposed to acoustic waves from the transducer 10 for a period of time that is determined to be therapeutically beneficial. Tests have indicated that benefit is provided by exposure for a period of time ranging from two seconds to one hour, with better results provided by exposure for a period of time ranging from fifteen minutes to forty-five minutes. A range of twenty minutes to thirty minutes is preferred, and an exposure lasting approximately twenty-five minutes appears to provide optimal results. It appears further that, for better results, the treatment should be repeated over time on a weekly or perhaps monthly basis, until the symptoms disappear permanently.

The method of the present invention has been tested on more than fifteen people suffering from musculoskeletal connective tissue disorders. Most of those tested experienced a significant reduction in pain. Arthritis sufferers, for example, experienced decreased pain and increased mobility, including for example the ability to make a fist.

It should be noted further that good results have been achieved in certain instances by having a person 18 place the afflicted portion of his or her body in the liquid in the container 12. In one embodiment, the container 12 may be made in a jacuzzi or bath size (or may actually be a jacuzzi), with persons 18 sitting in the container 12 for treatment. It is believed that such a method would be particularly beneficial for burn victims and the like. When practicing such a method, it is possible for a person 18 to be positioned extremely close to the transducer 10, even less than a distance of one foot.

Although a particular embodiment of the invention has been described in detail for purposes of illustration, various modifications may be made without departing from the spirit and scope of the invention. Accordingly, the invention is not to be limited, except as by the appended claims.

I claim:

1. A method for treating inflammatory musculoskeletal connective tissue disorders comprising the steps of:
   providing a low frequency sonic transducer;
   immersing said low frequency sonic transducer in an interior of a liquid-containing container and below an upper surface of a liquid in said liquid-containing container;
   positioning a person having an inflammatory musculoskeletal connective tissue disorder a therapeutically beneficial distance from said container; and
   exposing said person for a therapeutically beneficial period of time to acoustic waves from said low frequency sonic transducer at a therapeutically beneficial frequency;
   wherein said therapeutically beneficial frequency is between approximately four hundred and eight hundred Hertz.

2. The method of claim 1 wherein said therapeutically beneficial distance is approximately one foot from said container.

3. The method of claim 1 wherein said therapeutically beneficial distance is approximately five feet from said container.

4. The method of claim 1 wherein said therapeutically beneficial distance is approximately ten feet from said container.

5. The method of claim 1 wherein said therapeutically beneficial distance is approximately twenty feet from said container.

6. The method of claim 1 wherein said therapeutically beneficial period of time is between approximately two seconds and one hour.

7. The method of claim 6 wherein said therapeutically beneficial period of time is between approximately fifteen minutes and forty-five minutes.

8. The method of claim 7 wherein said therapeutically beneficial period of time is between approximately twenty minutes and thirty minutes.

9. The method of claim 8 wherein said therapeutically beneficial period of time is approximately twenty-five minutes.

10. The method of claim 1 wherein said therapeutically beneficial frequency is approximately 600 Hertz.

11. A method for inflammatory musculoskeletal connective tissue disorders comprising the steps of:
    providing a low frequency sonic transducer;
    immersing said low frequency sonic transducer in an interior of a liquid-containing container and below an upper surface of a liquid in said liquid-containing container;

positioning a person having an inflammatory musculoskeletal connective tissue disorder a therapeutically beneficial distance from said container; and exposing said person for between approximately fifteen minutes and forty-five minutes to acoustic waves from said low frequency sonic transducer at approximately six hundred Hertz.

12. The method of claim 11 wherein said person has arthritis.

13. The method of claim 11 wherein said person has polymyositis.

14. The method of claim 11 wherein said person has one of muscle cramps, muscle spasms, and muscle tension.

15. The method of claim 11 wherein said person has one of menstrual cramping and endometrial pain.

16. The method of claim 11 wherein said person has bursitis.

17. The method of claim 11 wherein said person has stress.

* * * * *